United States Patent
Inoue et al.

(10) Patent No.: US 9,597,476 B1
(45) Date of Patent: Mar. 21, 2017

(54) FLOW SENSOR AND METHOD

(71) Applicant: eVent Medical Ltd., Lake Forest, CA (US)

(72) Inventors: Kosuke Inoue, Corona Del Mar, CA (US); Teunis Van Den Berg, Yucaipa, CA (US); Bich Nguyen, Westminster, CA (US); Bonnievon Castillo, Anaheim, CA (US)

(73) Assignee: Event Medical Ltd., Lake Forest, CA (US)

( * ) Notice: Subject to any disclaimer, the term of this patent is extended or adjusted under 35 U.S.C. 154(b) by 0 days.

(21) Appl. No.: 14/734,854

(22) Filed: Jun. 9, 2015

(51) Int. Cl.
| | | |
|---|---|---|
| *G01F 1/37* | (2006.01) | |
| *A61M 16/08* | (2006.01) | |
| *A61M 16/00* | (2006.01) | |
| *G01F 1/44* | (2006.01) | |

(52) U.S. Cl.
CPC .... *A61M 16/0858* (2014.02); *A61M 16/0003* (2014.02); *A61M 16/0057* (2013.01); *G01F 1/44* (2013.01); *A61M 2016/0036* (2013.01); *A61M 2205/3331* (2013.01)

(58) Field of Classification Search
CPC ..... G01F 1/37; G01F 1/22; G01F 1/42; G01F 1/34; G01F 1/44
USPC .............. 73/861.52, 861.53, 861.61, 861.42, 73/861.64
See application file for complete search history.

(56) References Cited

U.S. PATENT DOCUMENTS

| | | | | |
|---|---|---|---|---|
| 4,290,314 A | * | 9/1981 | Geronime | ................. G01F 1/28 73/861.52 |
| 4,403,514 A | * | 9/1983 | Osborn | .................... G01F 1/36 600/538 |
| 4,932,269 A | * | 6/1990 | Cammarata, III | ..... A61B 5/087 128/204.23 |
| 4,989,456 A | * | 2/1991 | Stupecky | ............. A61B 5/0876 138/46 |
| 5,554,805 A | * | 9/1996 | Bahrton | ................... G01F 1/42 73/1.25 |
| 5,925,831 A | | 7/1999 | Storsved | |
| D413,825 S | | 9/1999 | Storsved | |
| 5,970,801 A | * | 10/1999 | Ciobanu | ............. A61B 5/0876 73/861.52 |
| 5,979,247 A | | 11/1999 | Kizawa | |
| 6,089,105 A | | 7/2000 | Ricciardelli | |
| 8,984,961 B2 | * | 3/2015 | Irani | ........................ G01F 1/44 73/861.52 |
| 2007/0107728 A1 | | 5/2007 | Ricciardelli et al. | |
| 2008/0119753 A1 | | 5/2008 | Ricciardelli et al. | |

FOREIGN PATENT DOCUMENTS

EP        1023576        8/2000

\* cited by examiner

*Primary Examiner* — Jewel V Thompson

(74) *Attorney, Agent, or Firm* — Knobbe, Martens, Olson & Bear, LLP

(57) ABSTRACT

A fluid flow sensor for use in measuring flow parameters in gas and other fluid applications, including patient ventilators and the like. The sensor is characterized by a lower pressure drop at higher flow rates in order to minimize patient effort in breathing.

10 Claims, 14 Drawing Sheets

FLOW SENSOR AND METHOD

BACKGROUND

Field

The present disclosure relates to an apparatus and method for determining the flow rate of a gas or liquid (e.g. any fluid) through an orifice. Certain embodiments relate to a sensor for determining flow rate through a fixed orifice positioned within a conduit or other flow path. Other embodiments could be applied to variable orifice devices. In one embodiment, the flow sensor is situated in the inhalation and exhalation circuit of a ventilator used in the breathing therapy of a patient.

Description of the Related Art

In current flow sensors, a resistance or obstruction is placed in the flow path in order to create a pressure differential. This pressure differential, or pressure drop, is used to calculate flow rate through the orifice placed in the flow path. However, it is currently believed that a high degree of resistance or obstruction is necessary in order to maximize the pressure drop in the flow path, thereby providing greater accuracy in the flow rate measurement.

As merely one example, in a respiratory measurement system, a flow sensor is placed in the air pathway of a respiratory device or ventilator used to assist a patient with breathing. However, the resistance generated by the flow sensor, and the resulting increase in pressure, increases the work or effort that the patient must exert in order to breath.

SUMMARY

In certain embodiments, it is desirable to provide a single flow sensor which can accurately measure pressure drop and flow rate over a wider range of flow rates. For example, at higher flow rates, a relatively larger pressure drop is easier to achieve, thereby providing good accuracy for the flow rate and pressure measurements. However, if the resistance is too great, or if the pressure drop is too large, the patient must exert a greater effort in breathing.

However, if the resistance is reduced, in order to reduce the patient's effort at larger flow rates, that same orifice may not generate sufficient pressure drop at lower flow rates in order to achieve an accurate measurement. Conversely, if the resistance profile of the orifice is increased at lower flow rates to generate a sufficient pressure drop, that same orifice cause an excessively high resistance at higher flow rates. Thus, there is a trade off in flow sensor design as it pertains to an application in breathing apparatus.

Accordingly, embodiments of the present disclosure relate to a fixed orifice profile which is sufficient to provide accurate pressure and flow rate measurements at both low flow rates and high flow rates. Principles of this disclosure are applicable to both fixed orifice flow sensors as well as variable flow sensors. Such principles also apply to all fluids, including air, gases, and liquids.

In one embodiment the flow sensor is applied to a respiratory therapy device such as a ventilator. In another embodiment, the flow sensor may be applied to a cardiac application, such as one in which the flow sensor measures flow rate and or pressure drop in a blood flow circuit. In yet another embodiment, the flow sensor may be applied to a water circuit in which the flow sensor measures flow rate and/or pressure drop in a water conduit.

In one embodiment, illustrated and described below in more detail, the flow sensor is applied to either an inhale and/or exhale circuit of a ventilator gas flow pathway. The gas may be air or another therapeutic gas, such as oxygen, or a mixture of gases designed to achieve a therapeutic purpose for the patient. In this embodiment, the sensor measures pressure drop or pressure differential between a leading pressure port and a trailing pressure port positioned within the sensor so as to be in the flow path. The sensor comprises a housing which forms a conduit with connectors at both the leading and trailing edges of the housing for inserting the sensor in the gas flow pathway. In another embodiment, the sensor can comprise an insert which is positioned within a separate conduit which forms the gas flow pathway. In the illustrated embodiment, the sensor can be positioned in the inhalation circuit or the exhalation circuit, or at the Y junction just before the gas flow enters or just as it leaves the patient.

The sensor measures pressure drop or pressure differential between two ports, a leading port and a trailing port, which are in fluid communication with the conduit of the sensor. Pressure drop or pressure differential is measured in accordance with Bernoulli's principle, which is well known and understood by persons of ordinary skill. In embodiments of the present disclosure, a pressure drop is induced within the flow pathway of the conduit by providing one or more forms of obstructions in the flow pathway. Such obstructions provide resistance to the flow, thereby inducing a measurable pressure differential. Based on this pressure differential, or "pressure drop," flow rate, flow velocity, flow volume, or other parameters of the fluid flow through the sensor can be determined. In general, the more accurately that a pressure differential can be measured, the more accurately flow parameters, such as flow rate, can be measured. Likewise, in general, a greater pressure differential or pressure drop yields a more accurate pressure measurement.

One advantage of the present sensor is that an accurate pressure differential can be measured over a wider range of flow rates as compared to existing or standard flow sensors used in conjunction with ventilators. In the context of the illustrated embodiments, this is an advantage, for example, in the ventilators used for adult patients versus pediatric patients. Clearly, the flow rate for adult breathing patterns is different from that of children or pediatric patients. Nevertheless, embodiments of the present disclosure can be used, and accurate flow measurements can be achieved at both high and low flow rates, with both adult and pediatric patients. In other embodiments, a flow sensor used for neonatal patients is disclosed.

Thus, the present flow sensor can be used in both adult/pediatric and neonatal ventilators to provide accurate flow parameter measurements over a wide range of flow rates, while not significantly increasing the patient's effort or energy required for breathing. In all cases, the flow sensor provides a pressure differential which is measurable and sufficiently accurate.

One of the more important flow parameters which is measurable by means of the present flow sensor is "flow rate." Flow rate may be more accurately referred to as flow volume inasmuch as it is generally measured in liters per minute. Pressure differential or pressure drop (PD), which is used to measure flow rate, is generally measured for purposes of the present disclosure in centimeters of water.

In the illustrated embodiments, the principles of the disclosure are applied to a fixed orifice flow sensor; however, they can also be applied to a variable orifice flow sensor by providing movable or adjustable obstructions in the flow pathway. In the present disclosure, the obstructions may comprise one or more of a geometric obstruction, a diametric obstruction, or a surface or boundary layer obstruction. In addition, the obstructions may be such that a venturi effect is induced in only a portion of the orifice or flow pathway, particularly that portion where the pressure ports are located. In other portions of the flow pathway, no venturi effect is induced or a relatively small effect is induced. In the illustrated embodiments, the obstructions which provide the venturi effect are desirable in one portion of the flow pathway but relatively less desirable in another portion of the flow pathway. These obstructions can be provided in both a cross-sectional dimension as well as a longitudinal dimension along the flow pathway. In a cross-sectional sense, the obstructions may be provided at generally right angles to the flow direction, and comprise vanes, fins, longitudinal obstructions, bumps, pumps, ridges, flanges, and the like. These obstructions may or may not be symmetrical. For example, they may be symmetrical in the cross-sectional dimension but not the longitudinal dimension. Conversely, the obstructions may be symmetrical in the longitudinal dimension but not the cross-sectional dimension. In one embodiment, multiple obstructions may be of both types. Thus, the principles of the present disclosure are not to be limited to the embodiments illustrated.

The obstructions provide a resistance profile for measuring pressure differential. In the embodiments illustrated, the resistance profile induces a venturi effect in at least a portion of the cross-sectional dimension or orifice of the airflow in the vicinity of the pressure ports. In these embodiments, the resistance profile is increased in this vicinity but reduced in other areas of the cross-sectional dimension in order to provide the desirable expansion in flow rate variability.

BRIEF DESCRIPTION OF THE DRAWINGS

The drawings illustrate certain exemplary embodiments of the present disclosure, and comprise the following.

DETAILED DESCRIPTION OF THE PREFERRED EMBODIMENTS

Figure 1:
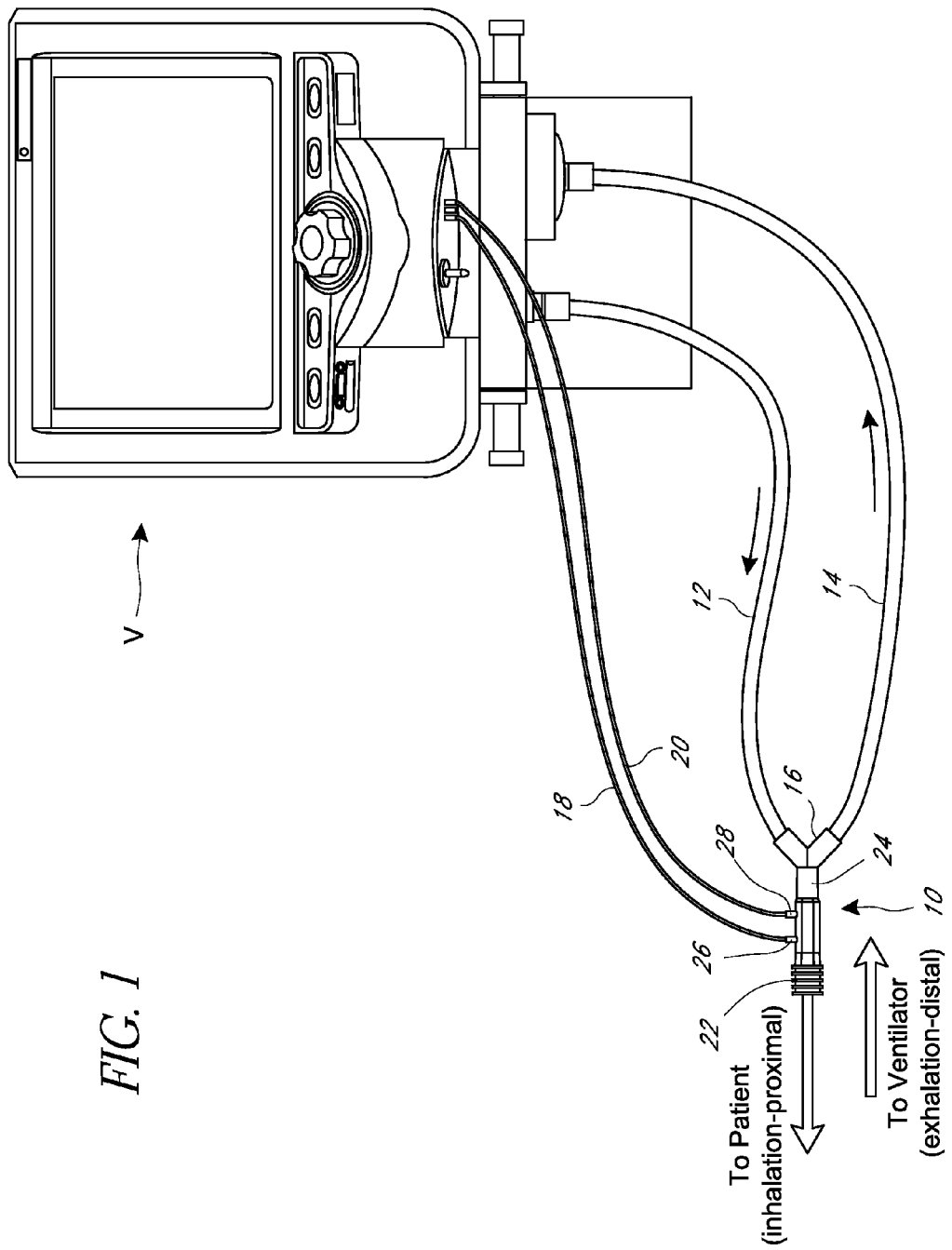
FIG. 1 is a perspective view of a ventilator illustrating one embodiment of the present flow sensor positioned in the Y connector of the flow circuit.

The following description of certain embodiments of the present disclosure are illustrative only and in accordance with the Figures referenced below. Persons of ordinary skill will recognize that other embodiments are within the scope of this disclosure and that this invention is not to be limited by the embodiments illustrated and described, but by the appended claims, and any future claims supported by this specification, whether issued in connection with this initial application or a future related application. Moreover, multiple embodiments are indeed described herein and illustrated in the drawings; thus confirming that various embodiments are within the scope of this disclosure.

Figure 15A:
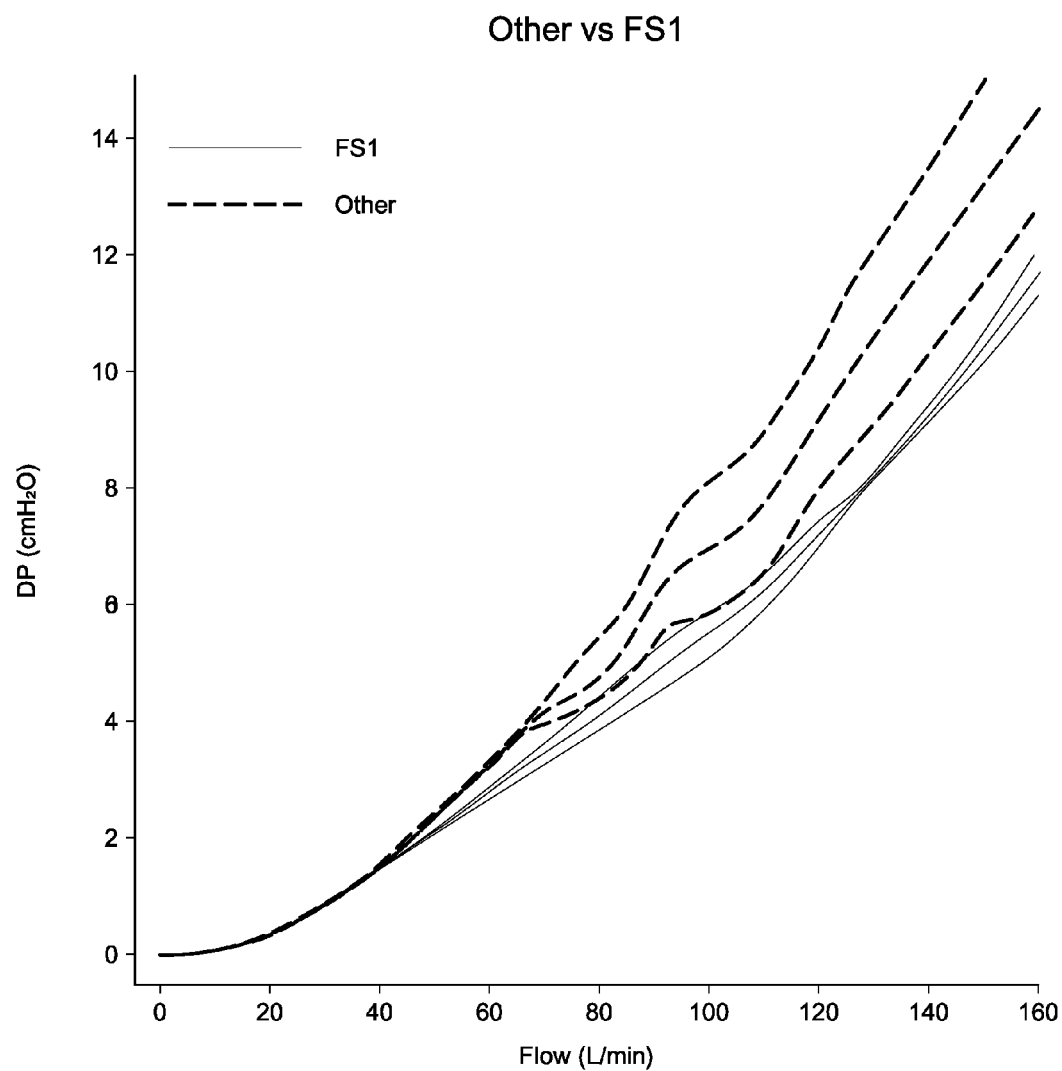
FIGS. 15A-15C are flow rate versus pressure differential (pressure drop) graphs for one embodiment of the present sensor, illustrating several sample measurements as compared to several sample measurements taken using a standard or existing flow sensor.
Figure 15B:
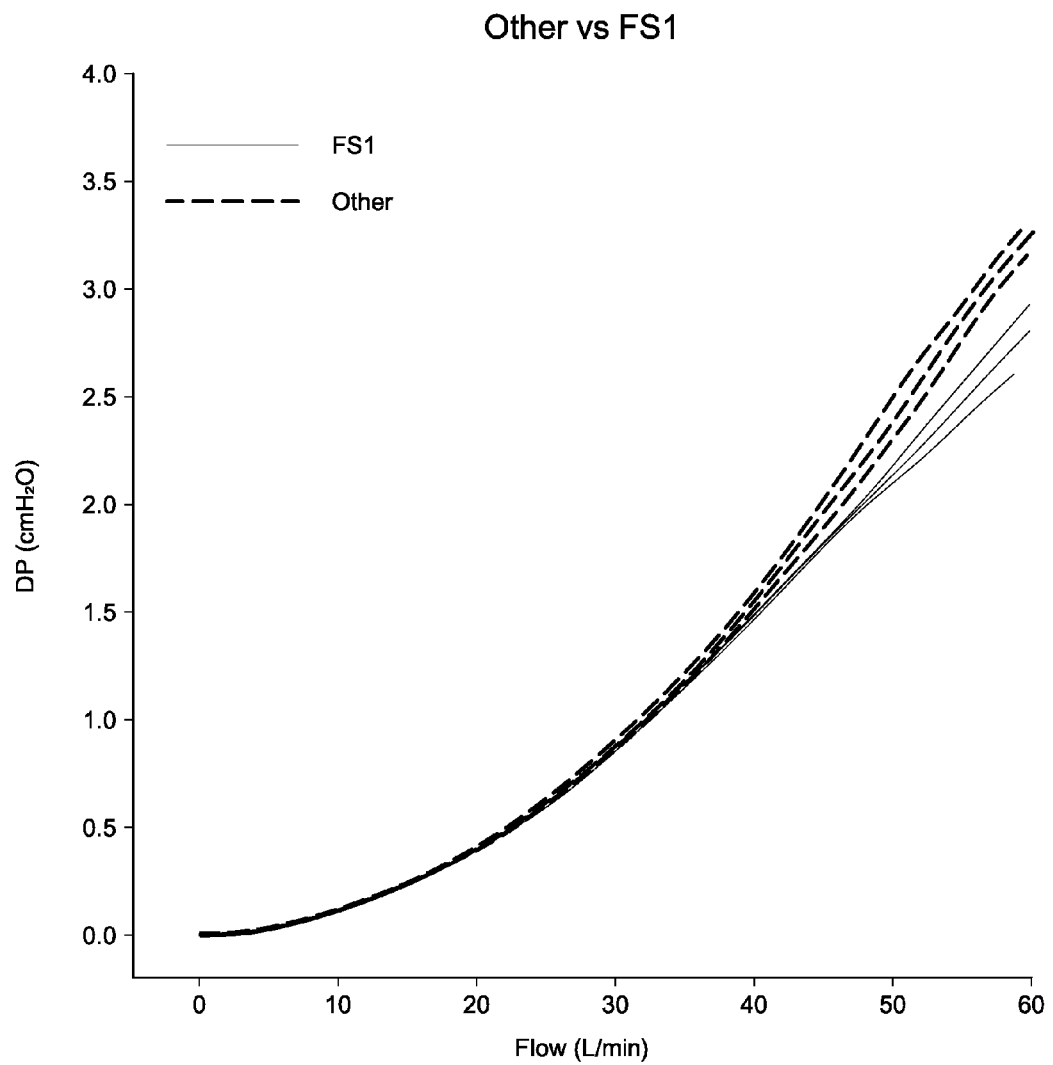
Figure 15C:
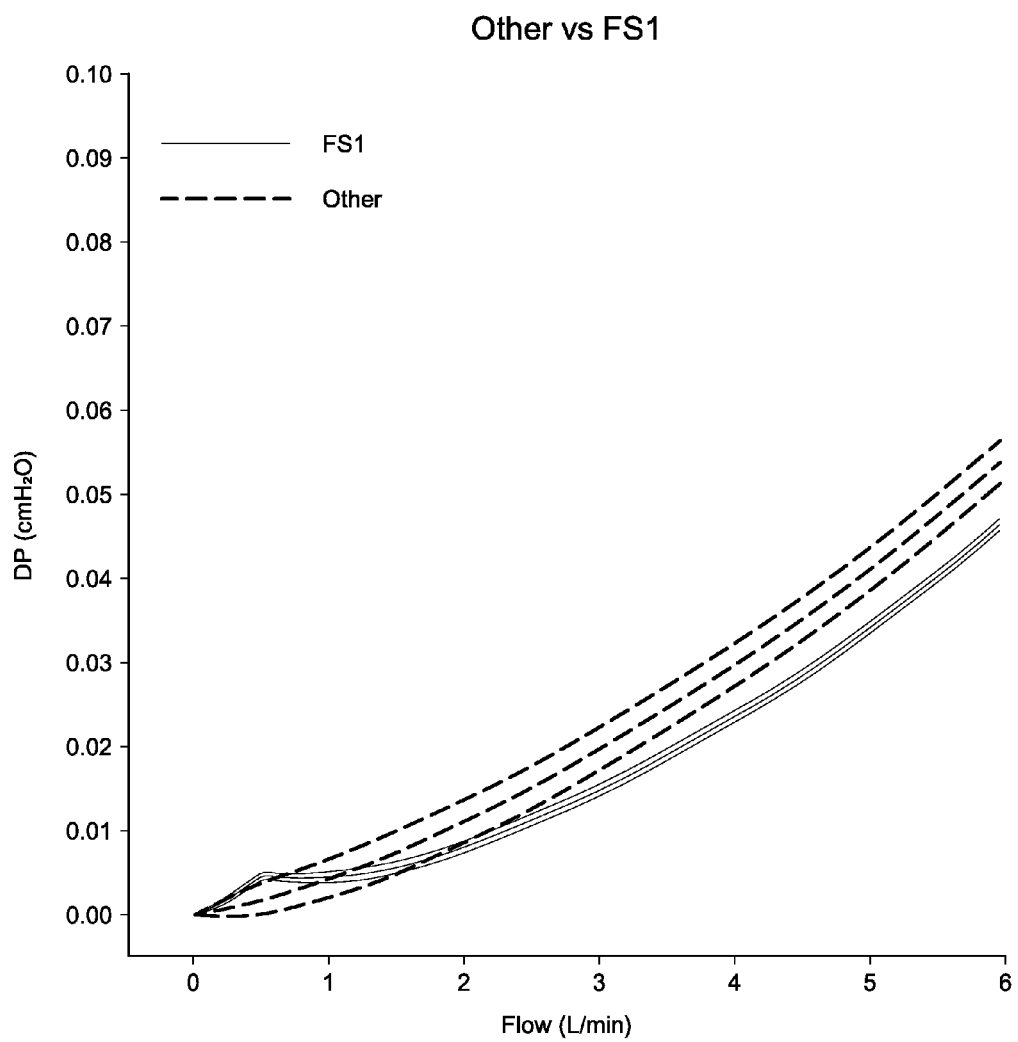

Some of the important advantages of the present flow sensor can be generally described as follows: At higher flow rates, the sensor exhibits a lower pressure drop in order to reduce the patient's effort in breathing. At the same time, for the same sensor having the same resistance profile and orifice configuration, it is desirable to have a relatively large pressure drop at lower flow rates in order to produce accurate measurements. Thus, as illustrated in FIGS. 15A-15C, the present flow sensor (FS1) provides accurate flow measurements over an expanded flow rate range. In these Figures, described below in more detail, there is illustrated a comparison between sample measurements of one embodiment of the sensor of the present disclosure as compared to sample measurements of flow rates taken using an existing or standard flow sensor ("other"). These Figures illustrate a flow rate profile (flow rate or flow volume versus pressure differential or "pressure drop" ("PD")) of the sensor of the present disclosure illustrating the fact that pressure differential is almost linear, which is generally regarded as advantageous. However, the flow rate profile of the present sensor, as illustrated in these Figures, shows that, at lower flow rates (less than about 15 L per minute), the slope of the flow rate curve is almost as steep as the existing sensor. This provides a measurable pressure differential sufficient to produce accurate flow parameter measurements. However, at higher flow rates (above about 15 or 25 L per minute), the slope of the flow rate profile is again about the same as the standard or existing flow sensor, but actually is reduced (less steep curve) as the flow rate rises above about 40 L per minute. This flow rate profile (lower pressure drop at higher flow rates), reduces the patient's effort in breathing at these flow rate ranges which can often be about 75 L per minute or even higher. Thus, a non-linear flow rate profile is advantageous.

FIGS. 15 A-15 C illustrate the surprising advantages of the various embodiments of the present disclosure. These Figures illustrate the testing of various samples of one embodiment and should not be considered limiting. Other embodiments in accordance with the present disclosure could produce the same or even improved results in terms of flow rate versus pressure differential profiles. While the exact mechanisms of action are not fully understood, it is believed that these advantageous results are derived from various unique orifice designs as disclosed herein. More specifically, they are derived from an orifice which has a greater venturi effect zone in the central regions, lower regions, or even central/lower regions of the orifice, while having a reduced venturi effect zone in the more peripheral regions of the orifice. These advantages could be achieved with the reverse: more venturi effect in the peripheral regions and less in the central regions of the orifice.

An orifice is a broad term and, as used herein, is entitled to its plain and ordinary meaning to a person to a person of ordinary skill in the art, and further means, without limitation, a cross-sectional dimension taken anywhere along the longitudinal axis of the flow sensor where the flow is restricted or obstructed for purposes of inducing a pressure differential or a pressure drop in the sensor. This longitudinal obstruction or restriction zone (including its cross-sectional characteristics or various orifice configurations taken along the longitudinal axis of the sensor and the restriction zone), referred to herein as a "restriction profile," restricts the fluid flow through the orifices of the sensor as the flow traverses the restriction zone of the sensor. These restrictions may comprise obstructions in both the cross-sectional dimension as well as the longitudinal dimension of the sensor as pointed out above.

Thus, the venturi effect in the orifice of the present sensor, in certain embodiments, is not symmetrical in the cross sectional dimension. Certain portions of the orifice restrict the flow greater than other portions in order to induce the desirable flow rate profile illustrated in FIGS. 15 A-15 C. In particular, in one embodiment, a greater venturi effect (higher velocity flow producing a lower downstream pressure and greater pressure differential) is induced along the flow stream where the pressure ports are situated. In addition, as illustrated in these Figures as well as in FIGS. 7-7 A, it is believed that certain surfaces of the restriction zone produce the flow rate profile desired. That is, certain edges or surfaces are considered aerodynamic, meaning rounded or smooth, while other edges or surfaces are sharp, pointed, or planar. While the mechanisms of action are not totally understood, these characteristics may create some boundary layer or edge effects which prevent the back flow of fluid from interfering with the pressure drop induced in the flow sensor.

Thus, the various embodiments of the present flow sensor, as illustrated and described herein, as well as others not illustrated, achieve these desirable advantages and are within the scope and spirit of the present invention.

Although the principles of the present disclosure apply to both adult/pediatric and neonatal flow sensors, separate sensors are contemplated in each situation. Thus, the flow rate curve of FIGS. 15 A-15 C illustrates a pressure drop profile over a typical flow rate range for an adult flow sensor used in a ventilator for treating an adult or pediatric patient. Nevertheless, the principles described and illustrated herein apply to sensors used for any patient. For example, generally speaking, the flow rate for an adult ventilator is 15 L per minute (LPM) to about 75 LPM or even higher. An exemplary lower flow rate is in the range of about 15 LPM to about 50 LPM, or alternatively about 15 LPM to about 25 LPM. A higher flow rate is in the range of 75 LPM or above.

More specifically, a neonatal ventilator patient may exhibit flow rates in the range of about 0 to 40 LPM. In a typical neonatal application the flow will vary between 0-10 LPM, however it can go up to 40 Lpm for pediatric applications. In an adult application the flow rate can vary between about 0-160 LPM. For other pediatric applications, the flow may vary between about 0-60 LPM or about 0-120 LPM which overlaps with adult range of about 0-160 LPM.

In one embodiment, a ventilator may be used in conjunction with either one of two flow sensors: one for adults and pediatric patients, and one for neonatal patients. This allows the ventilator application to provide better flow accuracy and flow rate measurement accuracy, minimum sensor dead space, and reduced sensor weight for each patient. It should be noted that some ventilator applications require a very narrow flow rate range for better accuracy; however for typical ventilation applications 2 sensors types are considered sufficient to accommodate the full ventilation spectrum of patients from adult to neonatal. It should also be noted that the flow and flow rate are not always constant during ventilation. The exhalation flow from the patient follows an exponential decay from any peak flow to close to zero. The inhalation flow depends on the ventilatory mode. A constant flow during inhalation is generally not a frequently used flow pattern. With these principles in mind, and with reference to the appended Figures, the embodiments of the present disclosure can be described in more detail.

As shown in FIG. 1, there is illustrated a typical ventilator V used to assist a patient in breathing. The principles of the present disclosure can be utilized in connection with any suitable ventilator. The flow sensor 10 of the present disclosure is preferably used in conjunction with the ventilator V in adult and/or pediatric applications. The sensor 10 is shown extending from the ventilator in a proximal direction toward the patient for eventual communication with a mask or nose piece (not shown) which is applied to the patient as it customary. Thus, for purposes of the present disclosure, "proximal" and "distal" are understood to be with respect to the patient (not shown). In this disclosure, proximal is away from the ventilator while distal is more proximate or closer to the ventilator. As illustrated in FIG. 1, the inhalation process is directed in an arrow in the proximal to direction, while exhalation is in the opposite or distal direction. Thus, the inhalation conduit 12 and exhalation conduit 14 are shown with arrows indicating the appropriate flow directions. FIG. 1 also illustrates proximal and distal connectors 22, 24 for connecting the sensor 10 in the flow circuit. Extending from the flow sensor 10 to the ventilator V are a pair of pressure differential conduits 18, 20. These conduits communicate the pressure differential or pressure drop observed in the sensor 10 to the ventilator where flow rate and other flow parameters can be calculated and displayed. These pressure differential conduits 18, 20 are respectively attached to two pressure differential ports 26, 28 extending from the flow sensor. These ports are used to measure the pressure differential or pressure drop induced in the flow sensor, and are described below in more detail in connection with FIGS. 2-5.

Flow sensor 10, as illustrated in FIG. 1, includes a proximal connector 22 which is standard in the industry for attachment to breathing apparatus. The flow sensor also includes a distal connector 24, shown in FIG. 1 as connected to a Y connector 16 or "Y piece." The sensor can be connected at the Y connector 16 or the Y piece in which it measures flow parameters for both inhalation and exhalation. However, the sensor can be located anywhere in the flow circuit, and can be used to measure flow parameters in only one direction or the other. Thus, the cross-sectional geometry or orifice of the sensor 10 is symmetrical with respect to flow direction and induces a pressure drop that is substantially equal in either direction. This is true as to the embodiments illustrated, but may be otherwise in other embodiments. In the illustrated embodiment, the sensor is symmetrical in the longitudinal dimension over the entire length of the restriction zone of the sensor. However, within the orifice cross section, at least along one axis, the cross-sectional dimension is asymmetrical.

Figure 1A:
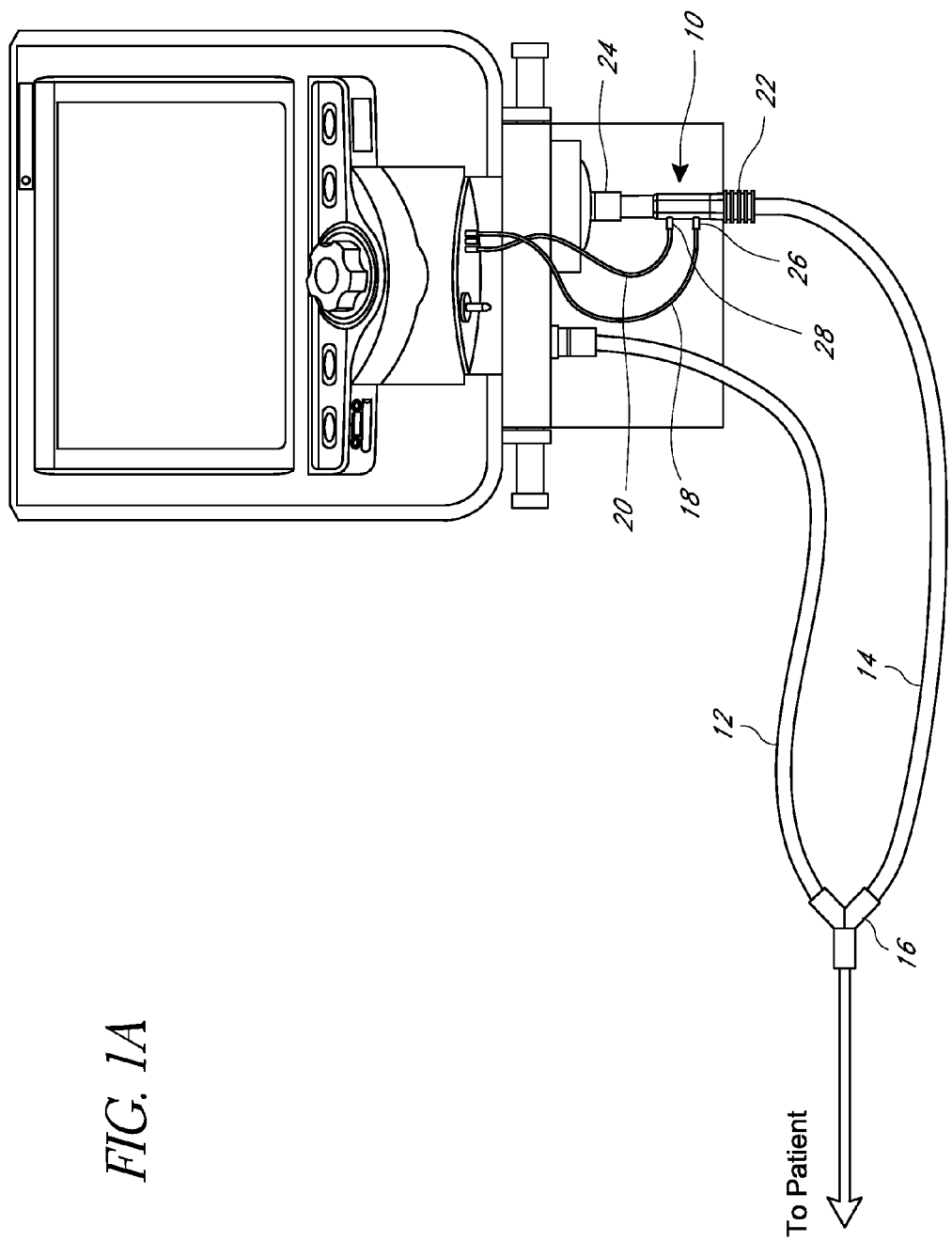
FIG. 1A is a perspective view of a similar ventilator with the present flow sensor positioned only on the exhale or inhale side of the flow circuit.

Flow sensors are frequently connected on the exhalation side 14 of the flow circuit as illustrated in FIG. 1A. Thus, the proximal pressure port 26 of the flow sensor 10 is typically the "leading report" while the distal port 28 is typically the "trailing port." In most cases, for purposes of pressure differential measurement, it is not important where the flow sensor is located, and the same or similar PD measurements are typically obtained whether the sensor is connected in the inhalation circuit or the exhalation circuit or at the Y connection as described above.

Figure 2:
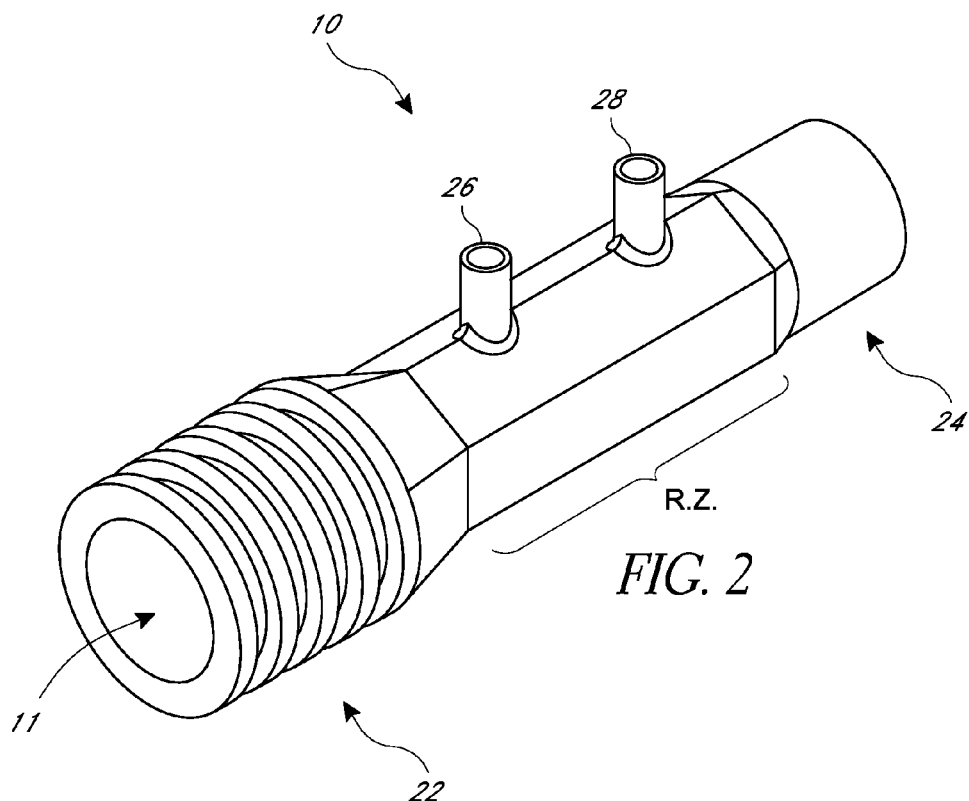
FIG. 2 is a perspective view of the flow sensor, comprising a housing with connectors to enable the sensor to be positioned within the flow circuit.

Referring to FIG. 2, there is shown a perspective view of the flow sensor 10 of FIG. 1. The proximal and distal connectors 22, 24 are illustrated together with the two pressure differential ports 26, 28 or pressure ports extending upwardly from the flow sensor. FIG. 2 illustrates t a central longitudinal region of the flow sensor, which comprises the flow restriction zone (or simply "restriction zone" or "RZ"), which induces the pressure drop in the sensor. "Flow restriction zone" or "restriction zone" is a broad term and is entitled to its plain and ordinary meaning to a person of ordinary skill in the art, and further means, without limitation, a longitudinal portion of the flow sensor which has various obstructions or restrictions for inducing a pressure drop in the sensor, in accordance with the venturi effect. In the embodiment of FIG. 2, there is shown in the flow restriction zone RZ, an outer or circumferential geometric shape which is hexagonal. This hexagonal configuration is restrictive of the flow when compared to the larger diameter conduits leading into the flow sensor, which comprise circular or cylindrical conduits 12, 14 and the connectors 22, 24. This hexagonal cross-sectional dimension in the RZ would generally be considered as non-aerodynamic. Moreover, this hexagonal configuration advantageously provides a self-cleaning aspect to the sensor 10. In existing sensors, mucous from a patient's lungs can build up on the continuously curved side walls of the sensors in which the cross-sectional configuration is circular. In the present design, the interior or inside "corners" of the hex shape make it more difficult for mucous to adhere to the interior surfaces of the RZ of the sensor. Thus, a small gap may form between the mucous and the corner of the sensor walls. As velocity in the RZ increases due to the venturi effect (enhanced at least in part due to the restrictions provided by the hexagonal circumferential shape of the RZ), it is believed that the flow itself causes the mucous membrane to separate from the wall in the regions of the corners and be flushed downstream, thus providing a self-cleaning aspect in the sensor 10. As noted, other non-circular cross-sectional shapes in the RZ may also achieve this effect, such as square, triangular, pentagonal, etc.; however, the present hex shape is currently preferred.

Figure 3:
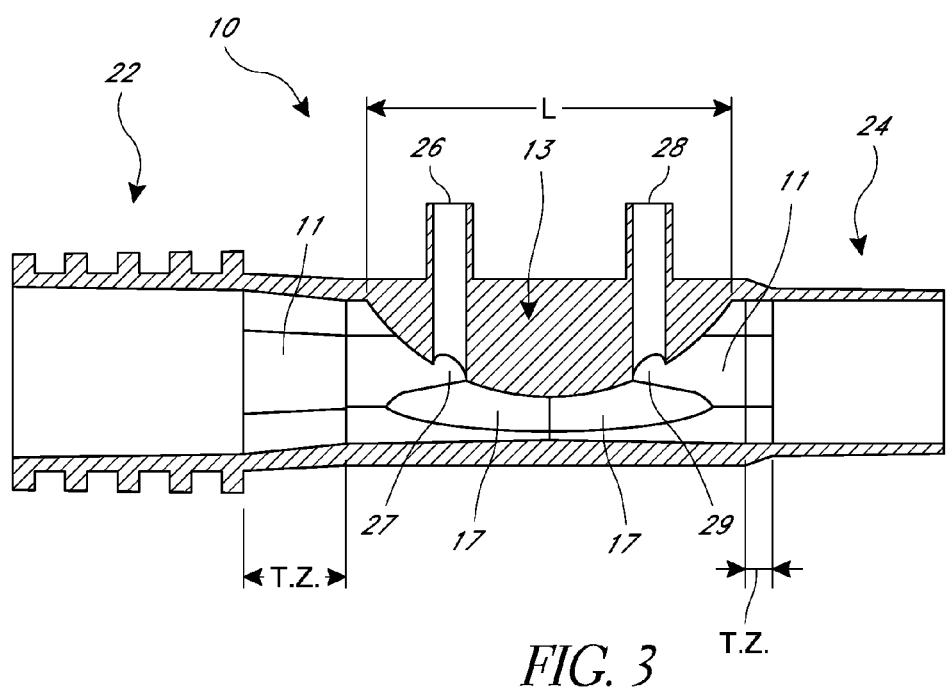
FIG. 3 is a longitudinal cross-sectional view of the flow sensor of FIG. 2, and the cross-section is taken along lines 3-3 of FIG. 9.

FIG. 3 illustrates a longitudinal cross-section of the flow sensor of FIG. 2 and illustrates in more detail the flow restriction zone RZ in the central region of the flow sensor. As illustrated, the flow restriction zone RZ has a non-circular cross-section and, in fact, results from a transition zone (TZ) in both the proximal and distal directions from a circular cross-sectional configuration to an outer or circumferential geometric configuration which may be hexagonal or some other geometric shape.

Again, the pressure differential ports 26, 28 are shown in FIG. 3 extending into the orifice 11 of the sensor 10. Shown prominently in FIG. 3, and cross-section, is the central obstruction 13. It should be noted that the term "central" should not be considered limiting and is used only for convenience in describing this embodiment. As noted above, other obstructions of varying shapes could be placed in the restriction zone, in various radial or circumferential locations, to achieve the advantages of the present disclosure. The length, L, of the central obstruction 13, in one embodiment, is about 1.34 inches. It should be noted, in connection with the present disclosure, that all dimensions are approximate or "about" and are expressed in inches. Also shown is one surface of a lower obstruction 17, which together with another lower obstruction 15, is described in more detail below. Again, the term "lower" is not to be considered limiting but is used for convenience in describing this embodiment, and could be situated to the side or even in the upper regions of the orifice. FIG. 3 advantageously illustrates the non-symmetrical orifice 11 of the present sensor while at the same time illustrating how a venturi effect is induced in the restriction zone RZ of the sensor to produce a measurable pressure drop.

Figure 4:
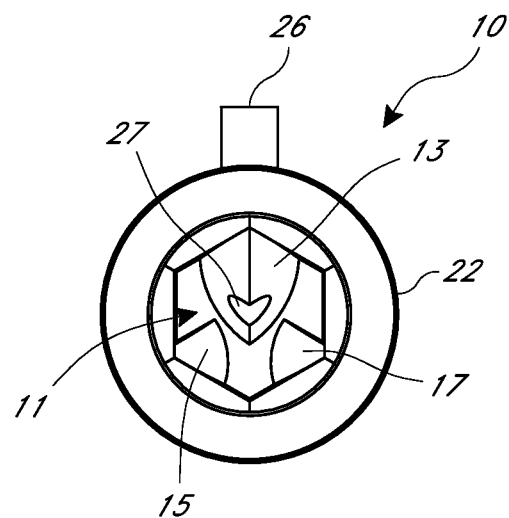
FIG. 4 is an end view of the flow sensor of FIG. 2 looking at the proximal or patient end view of the sensor.

FIG. 4 illustrates a proximal end view of the flow sensor 10 of FIG. 2. This Figure illustrates the restriction profile of the orifice 11 as seen from the proximal end of the flow sensor as seen from the proximal connector 22. The hexagonal cross-section of the orifice 11 is clearly illustrated. The larger central obstruction 13 in the orifice 11 is also illustrated and shows the lower opening 27 of the proximal pressure differential port 26. Left and right lower obstructions 15, 17 are also illustrated. As pointed out above, these obstructions (together with obstruction 13) can comprise vanes, fins, mounds, bumps, humps, or other longitudinal and cross-sectional obstructions to the flow. These are illustrated in more detail below in connection with FIGS. 7 and 7a. Advantageously, the lower obstructions 15, 17 do not exhibit the same configuration but are mirror images of one another, as described below in more detail, nor are they symmetrical in the cross sectional dimension.

Figure 5:
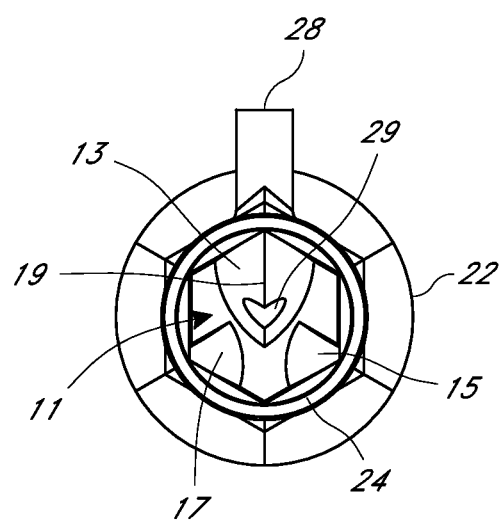
FIG. 5 is an end view of the sensor of FIG. 2 looking at the distal or ventilator and of the sensor.

FIG. 5 is a distal end view of the flow sensor of FIG. 2. It illustrates the distal connector 23 and the distal pressure port 28, with its opening 29 into the orifice 11 shown. FIG. 5 also illustrates an edge or seam 19 extending longitudinally along the length of the central obstruction 13.

Figure 6:
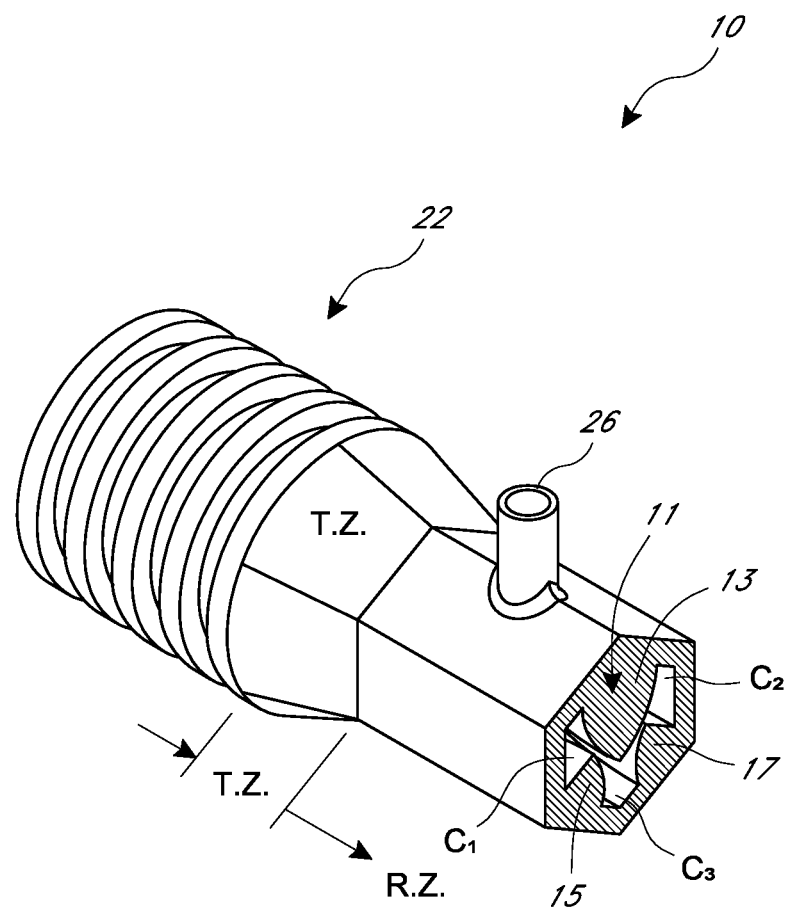
FIG. 6 is a partial perspective view of the flow sensor illustrating a cross-sectional view taken along lines 7-7 of FIG. 8.

FIG. 6 is a cross-sectional view of the flow sensor 10 of FIG. 2 taken through the flow restriction zone RZ, and illustrates the proximal connector 22, the proximal pressure port 26, the hexagonal transition zone TZ and a single orifice 11 configuration of the present disclosure. Also shown in FIG. 6 are various cavities C1, C2, and C3, formed in the orifice 11 of the sensor. These cavities C are formed by the absence of obstructions in the orifice 11, and allows for the fluid to flow through the sensor.

Figure 7:
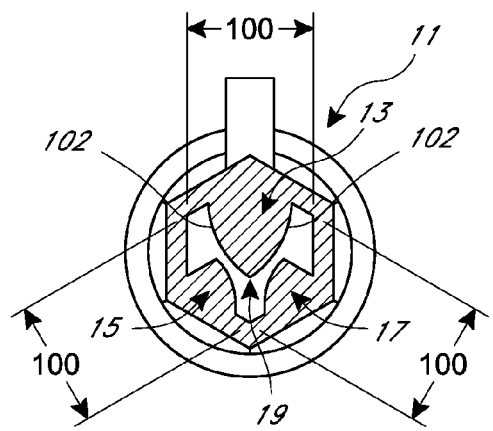
FIG. 7 is a cross-sectional view of the flow sensor of FIG. 2 taken along lines 7-7 of FIG. 8.

FIG. 7 is a similar cross-sectional view taken through the flow restriction zone RZ of the present sensor; however, it illustrates the configuration of one orifice 11 of the restriction profile at this point of the restriction zone. As shown in FIG. 7, the larger central obstruction 13 extends downwardly in the orifice 11 to a location slightly below the central longitudinal axis of the sensor 10. This obstruction 13 is laterally and longitudinally dimensioned so as to be aerodynamically shaped; however, the two aerodynamic sides come to a relatively sharp point which forms the edge, seam or apex 19 of the obstruction 13, as described above. This orifice 11 and obstruction 13 has about the following dimensions illustrated in FIG. 7:

100=0.437 in

102=radius of 0.335 in,

The lower or left and right obstructions or fins 15, 17 are also shown in FIG. 7 extending upwardly or radially into the orifice 11 of the sensor and generally toward the center of the orifice. These obstructions are characterized by one curved or aerodynamic surface intersecting a nonaerodynamic, second planar surface (which could be nonplanar or almost planar) to form a relatively sharp edge along the longitudinal dimension. The more aerodynamic surface of the obstructions 15, 17 has a radius, in this embodiment, of about 0.220 in. The less aerodynamic or planar surface of the fins 15, 17, preferably, in this embodiment, has a length of about 0.112 in. As illustrated in FIG. 7, this restriction profile creates a greater venturi effect in the central or central/lower regions of the orifice. At the same time, this flow restriction profile produces a reduced venturi effect in the upper left and upper right cavities C1, C2 of the orifice. Thus, at higher flow rates, it is believed that these characteristics actually reduce the pressure drop and alleviate the expenditure of energy in patient breathing.

Certain exemplary dimensions are illustrated in FIG. 7. It should be noted that, throughout this disclosure, the dimensions provided are illustrative or exemplary only, and represent merely the embodiments illustrated in the present disclosure. They are not to be considered limiting. In addition, all such dimensions are subject to manufacturing tolerances, which in most cases are + or − about 0.005 or about 0.003 inches. All such dimensions are expressed in inches.

Figure 7A:
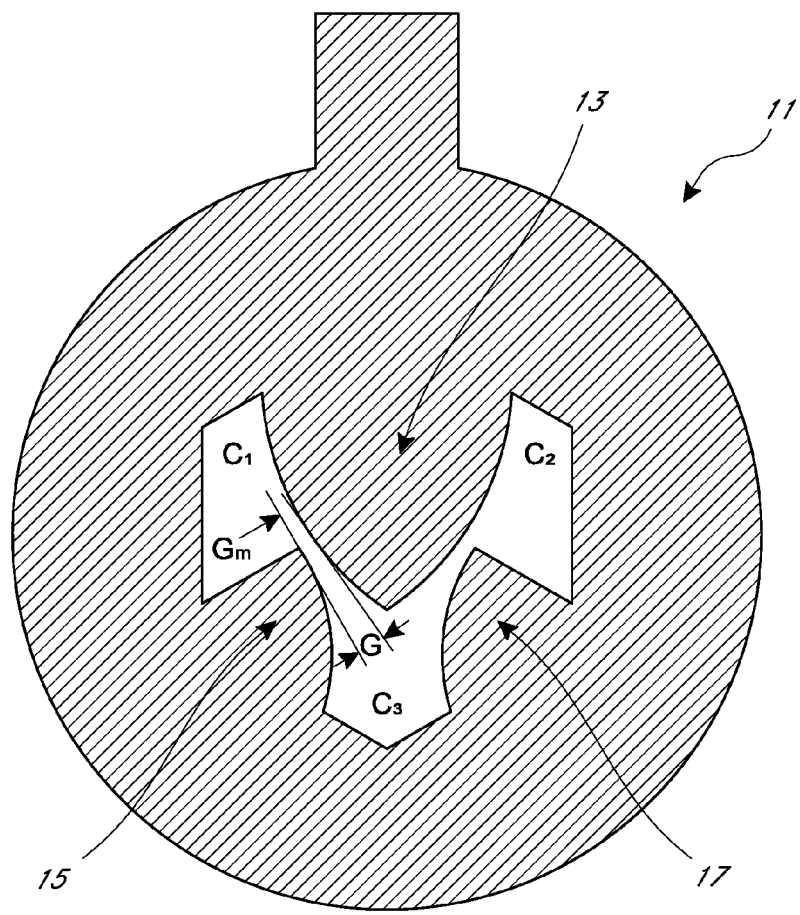
FIG. 7A is a close-up schematic view illustrating the orifice and obstruction geometry of the sensor.

FIG. 7A is a schematic drawing which illustrates some of the advantageous features of the present sensor. For example, FIG. 7A illustrates the greater venturi effect observed in the central region of the orifice 11, as opposed to the reduced venturi effect which it is believed is observed in the regions of cavities C1 and C2. The obstructions 13, 15, 17 are s shown extending inwardly radially to form at least one gap "G" in the orifice, one of which is labeled Gm in FIG. 7A to designate the minimum length of the gap between the larger obstruction and either of the lower obstructions. It will be observed that the gap G is not uniform in length or distance separating the fins, but varies in length along the interface between the two obstructions. The minimum gap Gm is preferably only about 1.0 mm. This minimum gap Gm is located about midway along the restriction zone RZ (see, for example, FIGS. 3 and 8; in FIG. 3 the obstruction 13 extends the greatest distance into the orifice 11). In other embodiments the gap is about 0.75 mm; 0.80 mm; 0.85 mm; and 0.90 mm. In still other embodiments, the gap G can be greater than 1.0 mm and, depending upon the application, be in the range of 1.0 mm-2.0 mm.

Also shown in FIG. 7A is the fact that the gap G varies in the cross-sectional plane as well, along the interface between the obstructions. In the embodiment illustrated, the gap grows wider as one progresses away from the orifice axis and toward the periphery into the cavity C3. A minimum gap Gm of about 1.0 mm is larger than minimum gaps found in existing or standard sensors, some of which are about half that distance. Having such a larger gap, in and of itself, tends to reduce the venturi effect based on gap alone. Thus, in the present sensor, this is compensated for by more drastic curvatures of the lower or side fins or obstructions 15, 17. This curvature of the aerodynamic (non-planar) surface of the lower or side obstructions produces a longer gap, as just noted, and reduces the area of the lower cavity C3 as compared to the upper cavities C1 and C2. Thus, a suitable venturi effect is still achieved in the central and/or lower regions of the orifice.

To further emphasize this point, reference is made to FIG. 3. The pressure port openings 27, 29 are situated along the lower edge or seam 19 of the obstruction 13. It is important to note that the lower pressure is measured in the trailing port (which could be 27 or 29). Thus, the more sensitive pressure measurements are made at these openings 27, 29; although, pressure will vary throughout the entire length and width of the flow restriction zone RZ. Pressure varies in accordance with the well know Bernoulli equation which is given as follows:

$$p_1 - p_2 = \frac{\rho}{2}(v_2^2 - v_1^2);$$

Since pressure varies with the square of the velocity, the velocity of the flow becomes an important factor in the design of the current sensor, and particularly at the trailing pressure port. In the embodiments described herein, and those within their inventive scope, a significantly increased velocity is induced at the trailing port as the flow passes under the obstruction 13, thus producing a lower pressure than at the leading port, a higher pressure differential between the two ports, and a resultant more accurate measurement. This increased velocity is achieved at least in part by the venturi effects disclosed herein and in connection with at least FIGS. 7A and 3.

In the embodiments shown in the Figures, the two ports are situated symmetrically along the flow restriction zone RZ. This is advantageous if flow rate needs to be measured bi-directionally. However, other pressure measurement configurations are within the scope of these concepts. Thus, it will be noted that the restriction profile is symmetrical in the longitudinal dimension but asymmetrical in the cross-section or orifice dimension.

The relatively larger gap shown in FIG. 7A also produces certain manufacturing advantages. First, the molds used in making the present sensors will yield more usable parts. With smaller gaps, where manufacturing tolerances were tighter, more defects were experienced, especially as the molds became heated during the molding process. Secondly, the present sensor can be manufactured with greater accuracy, thus providing sensors that are more consistent in their flow parameter measurements and easier to calibrate. This is also demonstrated in the graphs or curves of FIG. 15A-15C.

FIG. 7 A also illustrates the nonaerodynamic or planar surface of the left and right lower obstructions 15, 17. This planar surface meets the tangent of the aerodynamic surface of the lower obstructions at about a 90° angle, and forms an edge (which is also a non-aerodynamic surface). This planar surface (and the absence of further obstructions) provides for the slightly larger upper left and right cavities C1 and C2 of the orifice, thus reducing, to some extent, the venturi effect in these regions as compared to the central regions where the gap G is located. Lower cavity C3 is smaller in area than cavities C1 and C2. Although the areas of the these cavities vary along the length of the restriction zone, they remain the same relative to one another due to the longitudinal symmetry of the restriction zone.

Figure 8:
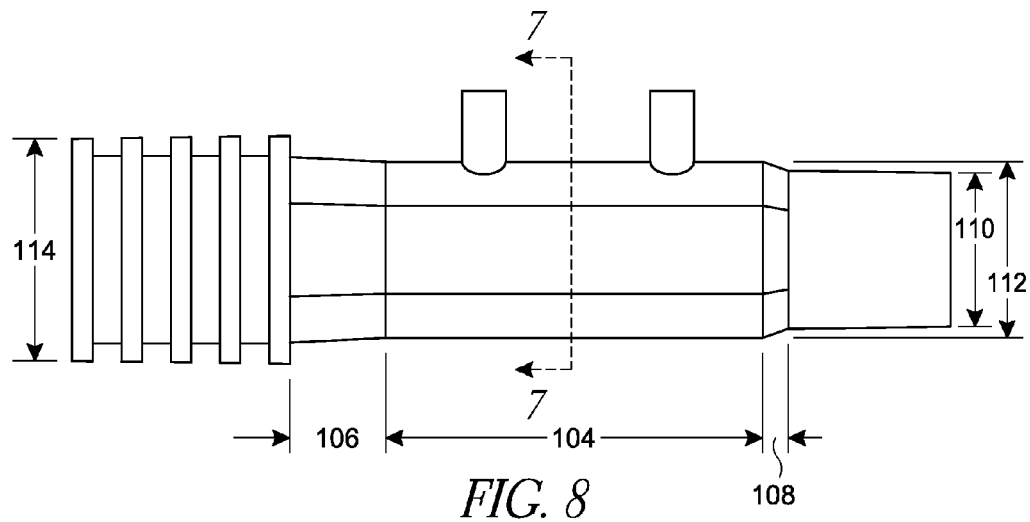
FIG. 8 is a side view of the sensor of FIG. 3.
Figure 9:
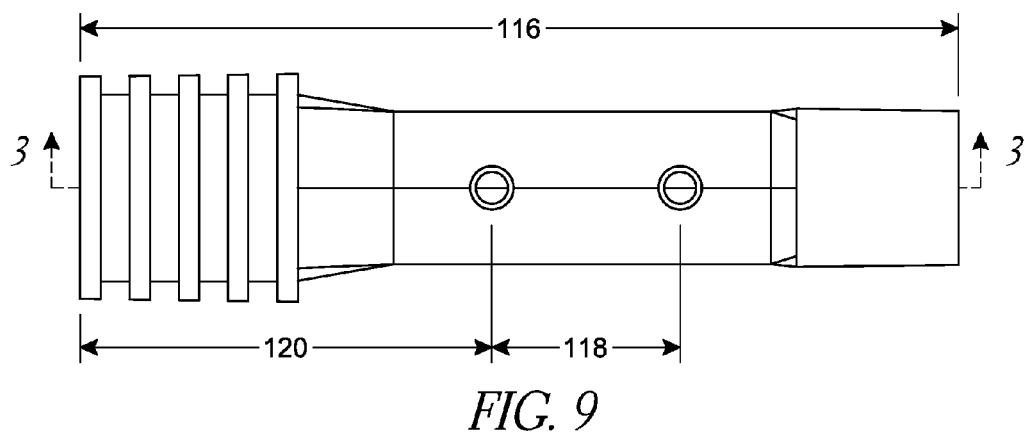
FIG. 9 is a top or plan view of the sensor of FIG. 2.

FIGS. 8 and 9 illustrate the specific dimensions of one embodiment of the present disclosure, in which the following reference numerals have the indicated dimensions:

104=1.47 in.

106=0.37 in.
108=0.10 in.
110=0.60 in.
112=0.69 in
114=0.866 in.
116=3.42 in.
118=0.732 in.
120=1.60 in.

Figure 10:
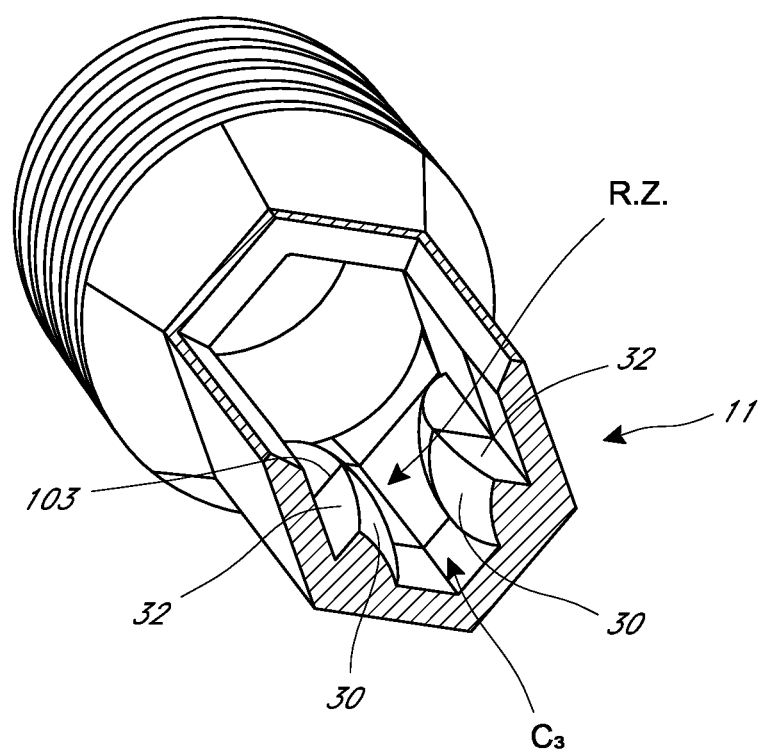
FIG. 10 is a partial perspective cutaway view of the sensor illustrating the internal geometry of the sensor, illustrating in partial view the resistance profile of the sensor provided by one or more obstructions in the flow pathway.

FIG. 10 illustrates both a longitudinal and cross-sectional view of a portion of the restriction zone RZ of the present sensor, illustrating that zone in which the large central obstruction is removed. Thus, the lower cavity C3 is shown more prominently. This FIG. 10 illustrates in greater detail the lower left and right obstructions 15, 17 including the combination of aerodynamic surfaces 30 together with nonaerodynamic, planar surfaces 32. The length 103 of the planar surface 32 at about the midline (where the mold separates, leaving a midline) is about 0.112 in. The hexagonal outer circumferential shape of the restriction zone RZ at the orifice 11 is also shown.

Figure 11:
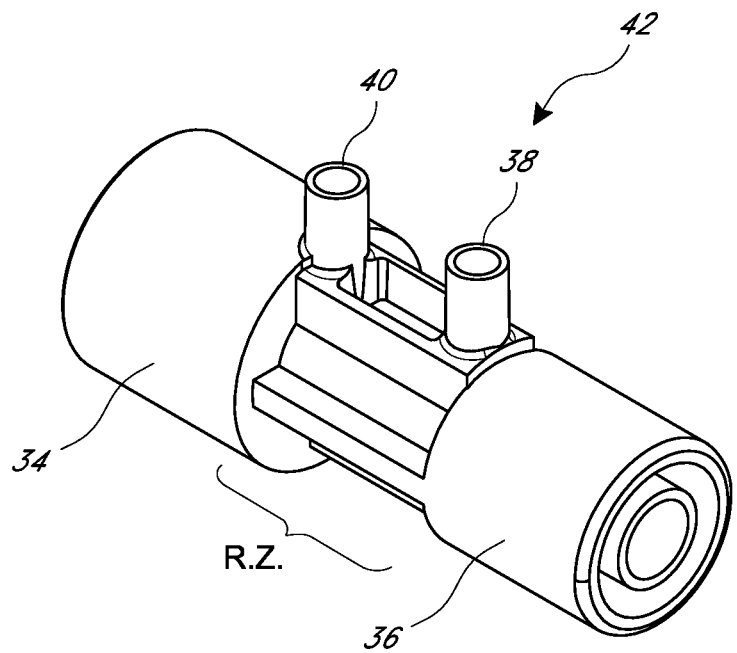
FIG. 11 is a perspective view of a neonatal sensor comprising an alternate embodiment of the present disclosure.
Figure 12:
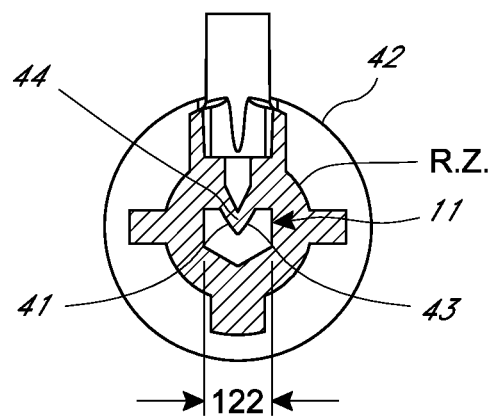
FIG. 12 is a cross-sectional view of the sensor FIG. 11 taken along lines 12-12 of FIG. 13.

FIGS. 11 and 12 illustrate another embodiment of the present sensor. In this embodiment, the flow sensor 42 is preferably configured for use in conjunction with a neonatal ventilator. With reference to FIG. 11, the flow sensor again has both proximal and distal connectors 34, 36, as well as two pressure differential ports 38, 40 extending from the flow sensor for connection to the pressure differential conduits leading to the ventilator. FIG. 11 also illustrates a shorter restriction zone RZ. However, as illustrated in FIG. 12, the orifice of this embodiment 42 has only a single and smaller central obstruction 44. The orifice 11 is only partially hexagonal, the width 122 being about 0.191 in. The central obstruction 44, which extends downwardly from the top of the flow sensor 42, is only very slightly aerodynamically shaped. In fact, it is essentially triangular and provides an open space in the orifice of about 12 mm2, or preferably about 11.97 mm2. The left and right surfaces 41, 43 of the obstruction 44 each have a radius of about 0.342 in. This orifice configuration provides measurable pressure drop at lower flow rates while reducing a newborn's effort inbreeding at higher flow rates.

Figure 13:
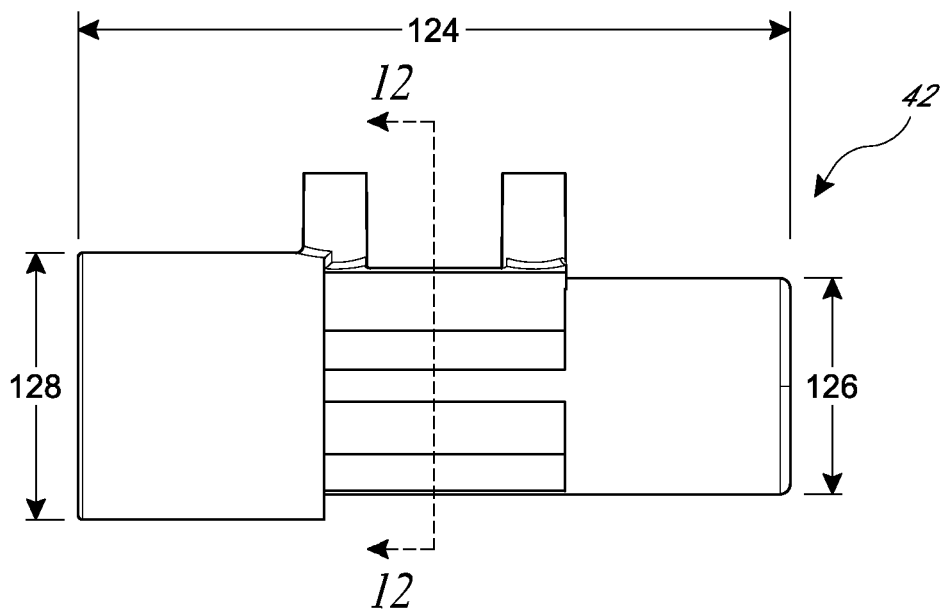
FIG. 13 is a side view of the neonatal sensor of FIG. 11.
Figure 14:
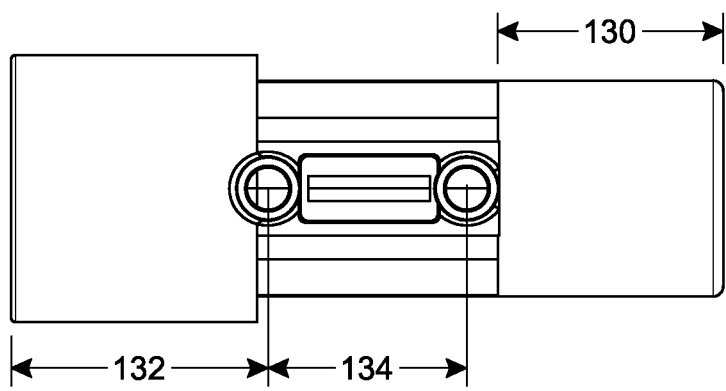
FIG. 14 is a top view of the neonatal sensor of FIG. 11.

FIGS. 13 and 14 illustrate the dimensions of one embodiment of a neonatal flow sensor 42, in which the following reference numerals have the indicated dimensions.
124=1.989 in.
126=0.609 in.
128=0.753 in.
130=0.636 in.
132=0.724 in.
134=0.560 in.

FIGS. 15 A-15 C illustrate flow rate versus pressure drop graphs of one embodiment of the present disclosure. This embodiment is illustrated in solid lines while the flow rate profile of an existing or standard flow sensor is shown in dotted lines. As shown in FIG. 15 A, the flow rate profile of the present sensor is very similar to that of the existing sensor at flow rates up to about 40 or 50 L per minute. However, at higher flow rates, the flow rate profile drops off such that the corresponding pressure drop is reduced as compared to that of the existing sensor. This advantageous characteristic allows the sensor to reduce the patient's effort in breathing at these higher flow rates. Likewise, as illustrated in FIG. 15 B, the flow rate profile of the present sensor is virtually identical to that of the existing sensor at flow rates below about 50 L per minute. Above about 50 L per minute, the slope of the flow rate curve drops off or reduces such that the corresponding pressure drop is reduced compared to that of the standard flow sensor. Nevertheless, as illustrated in FIG. 15 C, at lower flow rates, the pressure drop is similar to that of existing sensors and provides accurate measurements.

This is achieved, as illustrated in FIGS. 15A-15C, in embodiments of the flow sensor in which at lower flow rates a higher pressure differential is generated while at higher flow rates the pressure differential is gradually greater but non-linear. Therefore, it is desirable that the resistance profile provide a non-linear pressure drop profile so that accurate measurements can be obtained at both low flow rates and high flow rates, without significantly increasing patient effort at higher flow rates. Also, these Figures illustrate the desirable feature that there is less variance between various samples of the flow sensor, thus making it easier to calibrate with the ventilator.

FIGS. 16 A-16 C illustrate still further embodiments of the present flow sensor. These Figures illustrate schematically various orifice configurations which achieve the advantages of the present disclosure. Each of these embodiments is characterized by a greater venturi effect in the central region or lower/central region of the orifice and a reduced venturi effect in the other upper or upper/peripheral regions of the orifice. In each case, the central obstruction 13 extends into about the center of the hexagonal orifice while the left and right obstructions 15, 17 have various characteristics and configurations. In FIG. 16 A, the left and right obstructions 15, 17 are situated higher in the orifice, so as to more on the lateral sides, and not at the lower regions. They are also concave in shape and form a sharper point and longitudinal or linear edge. In this embodiment, relatively large peripheral cavities (C1, C2, and C3)) are formed in the orifice where flow is less restricted. In this case, cavities C1 and C2 are symmetrical and about the same size, while lower cavity C3 is larger. Thus, the venturi effects of this orifice in these peripheral regions are reduced compared with those of the central region of the orifice. It should also be noted that this disclosure is not limited to an outer or circumferential hexagonal configuration, but could include other geometric configurations which serve to restrict the flow to achieve the advantages described herein. Also, the greater venturi effects could be achieved in the peripheral regions of the orifice while leaving less restricted and lower venturi effects in the central regions of the orifice. This could be achieved, in one embodiment, by arranging multiple obstructions around the periphery of the orifice while leaving the central region of the orifice unobstructed.

With reference to FIG. 16 B, yet another embodiment of the orifice of the present sensor is disclosed. In this case, the left and right obstructions 15, 17 are more aerodynamically designed and comprise humps, mounds or bumps having rounded or convex surfaces. In this case, the peripheral cavities C1, C2 and C3 are about equal in volume. More notably, the gap between the central obstruction and left and right obstructions is greater than that shown in FIG. 7 A, and is, in one embodiment, approximately 2 times as much.

FIG. 16 C illustrates yet another embodiment of the present disclosure. In this case, the aerodynamic shape of the left and right obstructions is more pronounced resulting in larger open cavities C1, C2, and C3, in the peripheral regions. The obstructions comprise mounds or humps which are large enough, or which extend into the central region of the orifice, sufficient to provide a gap which is about the same as that described in connection with FIG. 7 A.

Figure 16A:
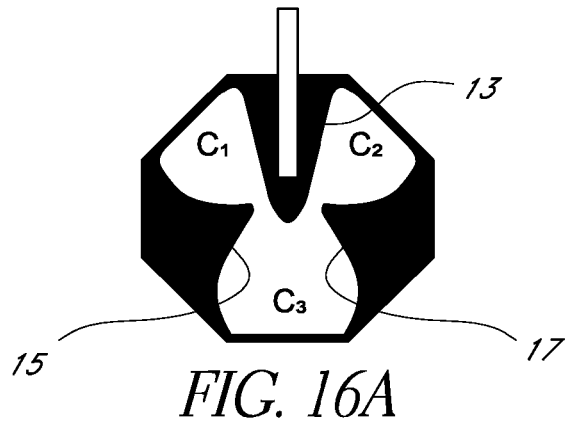
FIGS. 16 A-16 C illustrate alternate embodiments of the sensor in which various alternative resistance profiles can be utilized in accordance with the principles of the present disclosure.
Figure 16B:
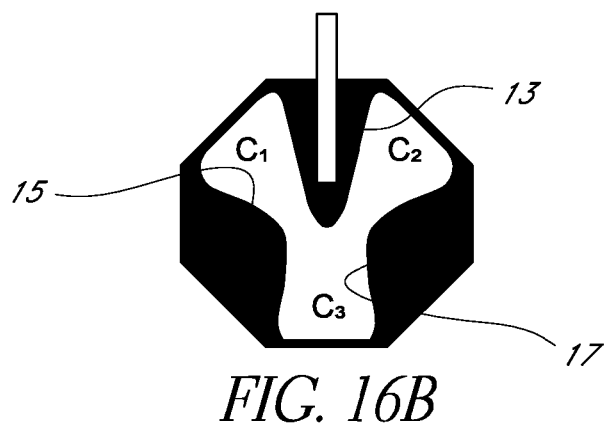
Figure 16C:
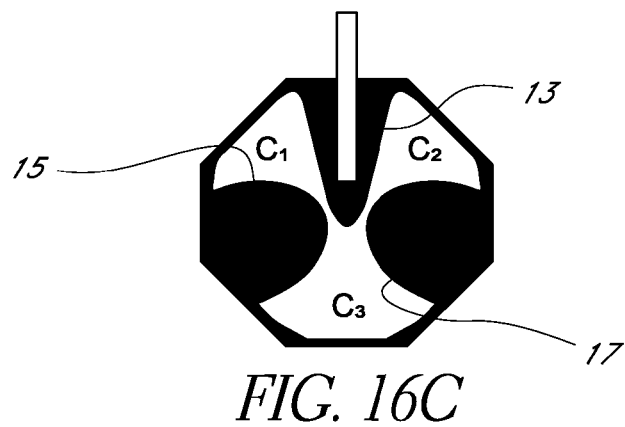

In these embodiments of FIGS. 16A-16C, a large pressure drop in the sensor makes it harder for the patient to breathe in and out, and particularly harder to exhale. Because it is undesirable to increase patient effort in order to monitor flow and volume, it is advantageous to increase pressure drop in the central or lower/central area of the orifice (cavity C3) but keep pressure drop to a minimum in other areas of the orifice (cavities C1 and C2) without sacrificing sensitivity in pressure drop measurements. In these embodiments, it is desirable for the flow sensor to exhibit a flow rate profile (pressure drop) in the range of about 4 L per minute to about 55 L per min which is as steep in slope or steeper than existing sensors, while reducing the steepness of the flow rate profile (lower pressure drop) in the flow rate range of higher than about 75 L per min. The sensor is provided in a kit (preferably a sterile pack) and which includes standard tubing, conduits, connectors and the like. The sensor can be configured for disposability, or for re-use through sterilization, autoclave, and the like.

In a method of manufacturing the flow sensor, the sensor is injection molded from a polycarbonate material. Such material allows the sensor to be manufactured inexpensively and to be disposable (single use or single patient use). In another embodiment, the sensor is injection molded, or manufactured in another suitable way, from a polysulphome material which allows the sensor to be removed from a flow circuit used with one patient, sterilized, and then reused with another patient. Sterilization can be achieved with either chemical means or an autoclave. In reusable embodiments, the autoclave can be in the range of 250 to 275° F. (121° C.2 134° C.). In other methods, ETO or cold sterilize procedures can be implemented.

The mold tooling or die is typically made from steel and portions undergo rapid thermal cycling, especially where there are tight tolerances such as in the restriction zone, orifice and gap areas. The high temperatures experienced in the tooling can cause the tooling to be subjected to annealing or thermal fracturing. Tooling can also experience premature wear at higher temperatures. Thus, in the sensor of the present design, with a larger gap compared to other industry sensors and greater manufacturing tolerances, higher temperature materials can be used in molding the sensor, thus increasing tool life. Furthermore, advantageously, these higher temperature sensor materials can allow for re-usability since they can undergo autoclave sterilization without degradation. Thus, in one embodiment, the gap G is significantly more than 0.5 mm, and in other embodiments it is 1.25, 1.5, and 2.0 times as great.

Thus, the scope of this disclosure is to be interpreted only in conjunction with the appended claims, and any future claims that are considered supported by this disclosure by one of ordinary skill in the art.

What is claimed is:

1. A flow sensor for measuring pressure differential in a patient ventilator, comprising:
    a longitudinal housing;
    first and second cylindrical ends forming connectors for connecting the sensor to fluid flow conduits;
    a longitudinal flow restriction zone in fluid communication with each of the first and second ends and having a hexagonal cross-sectional circumferential geometric shape which is different from each of the ends, the hexagonal flow restriction zone configured to form a plurality of planar surfaces intersecting one another at a plurality of corners, whereby increased flow velocity and turbulence in the flow restriction zone reduces the adherence of mucous to the flow sensor in the flow restriction zone to provide a self-cleaning effect;
    an orifice formed in the flow restriction zone and in fluid communication with the ends, the orifice comprising a plurality of fixed fins forming a cross-sectional restriction profile inducing a venturi effect in only the central portion of the orifice, the orifice being non-symmetrical about a horizontal axis through the cross-sectional restriction profile of the orifice, the orifice comprising:
    a first fin;
    second and third fins each having the same cross-sectional configuration and being smaller in cross-sectional dimension than that of said first fin, each of the second and third fins having one aerodynamic surface and one non-aerodynamic surface, the non-aerodynamic surface comprising a flow area of reduced restriction above the horizontal axis of the orifice whereby the orifice is non-symmetrical about said axis;
    a gap between one edge of the first fin and the closest edge of either second or third fin, the gap being at least about 1.0 mm in length;
    the orifice being symmetrical in a longitudinal direction with respect to fluid flow through it to form a bi-directional flow sensor; and
        two ports positioned in the sensor in the flow restriction zone and in fluid communication with the orifice at an opening in the first fin to measure pressure drop in the flow restriction zone.

2. The flow sensor of claim 1 wherein the venturi effect is induced also in the orifice below the horizontal axis.

3. The flow sensor of claim 1 wherein the venturi effect induced in the orifice is non-symmetrical with respect to the cross-sectional dimension of the orifice.

4. The flow sensor of claim 1 wherein the gap is less than 1.0 mm.

5. The flow sensor of claim 1 wherein each fin comprises any longitudinal and cross-sectional obstruction to the flow.

6. The flow sensor of claim 1 further comprising at least one cavity in the orifice where the venturi effect is reduced.

7. A flow sensor for measuring pressure differential in a patient ventilator, comprising:
    a longitudinal housing;
    first and second cylindrical ends forming connectors for connecting the sensor to fluid flow conduits;
    a longitudinal flow restriction zone in fluid communication with each of the first and second ends and having a hexagonal cross-sectional circumferential geometric shape which is different from each of the ends, the hexagonal flow restriction zone configured to form a plurality of planar surfaces intersecting one another at a plurality of corners;
    an orifice formed in the flow restriction zone and in fluid communication with the ends, the orifice comprising a plurality of fixed fins forming a cross-sectional restriction profile inducing a venturi effect in the orifice, the orifice being non-symmetrical about a horizontal axis through the cross-sectional restriction profile of the orifice, the orifice comprising:
    a first fin;
    second and third fins each having the same cross-sectional configuration and being smaller in cross-sectional dimension than that of said first fin, each of the second and third fins having one aerodynamic surface and one non-aerodynamic surface, the non-aerodynamic surface comprising a flow area of reduced restriction above the horizontal axis of the orifice whereby the orifice is non-symmetrical about said axis;
    a gap between one edge of the first fin and the closest edge of either second or third fin, the gap being at least about 0.75 mm in length; and two ports positioned in the sensor in the flow restriction zone and in fluid communication with the orifice to measure pressure drop in the flow restriction zone.

8. The flow sensor of claim 7 wherein the gap is at least about 1.0 mm.

9. The flow sensor of claim 7 wherein the venturi effect induced in the orifice is non-symmetrical with respect to the cross-sectional dimension of the orifice.

10. The flow sensor of claim 7 further comprising at least one cavity in the orifice where the venturi effect is reduced.

* * * * *

UNITED STATES PATENT AND TRADEMARK OFFICE
CERTIFICATE OF CORRECTION

PATENT NO. : 9,597,476 B1  
APPLICATION NO. : 14/734854  
DATED : March 21, 2017  
INVENTOR(S) : Kosuke Inoue Page 1 of 1

It is certified that error appears in the above-identified patent and that said Letters Patent is hereby corrected as shown below:

In the Specification

In Column 1 at Line 61, Change "and or" to --and/or--.

In Column 6 at Line 1, Change "Lpm" to --LPM--.

In Column 8 at Line 45, After "13" insert --.--.

In Column 11 at Line 44, Change "dimensions." to --dimensions:--.

In Column 13 at Line 22, Change "polysulphome" to --polysulphone--.

In Column 13 at Line 27, Change "C.2" to --C2--.

Signed and Sealed this  
Twelfth Day of September, 2017

Joseph Matal  
*Performing the Functions and Duties of the*  
*Under Secretary of Commerce for Intellectual Property and*  
*Director of the United States Patent and Trademark Office*